(12) United States Patent
Li et al.

(10) Patent No.: US 7,532,389 B2
(45) Date of Patent: May 12, 2009

(54) FLUORINATED SILICON PHTHALOCYANINES AND NAPHTHALOCYANINES FOR ELECTROPHORETIC DISPLAY

(75) Inventors: Ying-Syi Li, San Jose, CA (US); Jin Yang, San Jose, CA (US); Rong-Chang Liang, Cupertino, CA (US)

(73) Assignee: Sipix Imaging, Inc., Fremont, CA (US)

( * ) Notice: Subject to any disclaimer, the term of this patent is extended or adjusted under 35 U.S.C. 154(b) by 0 days.

(21) Appl. No.: 12/203,039

(22) Filed: Sep. 2, 2008

(65) Prior Publication Data
US 2008/0316583 A1   Dec. 25, 2008

Related U.S. Application Data

(62) Division of application No. 10/439,428, filed on May 15, 2003, now abandoned.

(60) Provisional application No. 60/381,263, filed on May 17, 2002.

(51) Int. Cl.
*G02B 26/00* (2006.01)
*G09G 3/34* (2006.01)
*G03G 17/04* (2006.01)

(52) U.S. Cl. .................. 359/296; 345/107; 430/32

(58) Field of Classification Search ............... 359/296; 345/107; 430/32; 204/600
See application file for complete search history.

(56) References Cited

U.S. PATENT DOCUMENTS

| | | | |
|---|---|---|---|
| 3,006,921 A | 10/1961 | Weinmayr | |
| 3,281,426 A | 10/1966 | Tiers | |
| 4,285,801 A | 8/1981 | Chiang | |
| 5,260,435 A | 11/1993 | Sawada et al. | |
| 5,378,589 A | 1/1995 | Sawada et al. | |
| 5,428,152 A | 6/1995 | Hayashida et al. | |
| 5,460,646 A * | 10/1995 | Lazzouni et al. | 106/31.34 |
| 5,930,026 A | 7/1999 | Jacobson et al. | |
| 5,932,721 A | 8/1999 | Yashiro et al. | |
| 5,961,804 A | 10/1999 | Jacobson et al. | |
| 6,914,713 B2 | 7/2005 | Chung et al. | |
| 6,927,892 B2 | 8/2005 | Ho et al. | |
| 6,958,849 B2 | 10/2005 | Chen et al. | |
| 7,052,766 B2 | 5/2006 | Zang et al. | |
| 7,110,162 B2 | 9/2006 | Wu et al. | |
| 2004/0030125 A1 | 2/2004 | Li et al. | |

FOREIGN PATENT DOCUMENTS

| | | |
|---|---|---|
| EP | 0 272 565 | 6/1988 |
| EP | 0 491 951 | 7/1992 |
| EP | 0 896 033 | 2/1999 |
| WO | WO 01/67170 | 9/2001 |
| WO | WO 02/01281 | 1/2002 |
| WO | WO 02/056097 | 7/2002 |
| WO | WO 02/065215 | 8/2002 |
| WO | WO 03/097747 | 11/2003 |

OTHER PUBLICATIONS

Allen, K. (Oct. 2003). Electrophoretics Fulfilled. *Emerging Displays Review: Emerging Display Technologies, Monthly Report—Octomber 2003*, 9-14.
Bardsley, J.N. & Pinnel, M.R. (Nov. 2004) Microcup™ Electrophoretic Displays. *USDC Flexible Display Report*, 3.1.2. pp. 3-12-3-16.
Bettelheim, et al., (1998) Introduction to General, Organic and Biochemistry, fifth edition, pp. 181-182.
Chaug, Y.S., Haubrich, J.E., Sereda, M. and Liang, R.C. (Apr. 2004). Roll-to-Roll Processes for the Manufacturing of Patterned Conductive Electrodes on Flexible Substrates. *Mat. Res. Soc. Symp. Proc.*, vol. 814, 19.6.1.
Chen, S.M. (Jul. 2003) The Applications for the Revolutionary Electronic Paper Technology. *OPTO News & Letters*, 102, 37-41. (in Chinese, English abstract attached).
Chen, S.M. (May 2003) The New Application and the Dynamics of Companies. *TRI*. 1-10. (In Chinese, English abstract attached).
Chung, J., Hou, J., Wang, W., Chu, L.Y., Yao, W., & Liang, R.C. (Dec. 2003). Microcup® Electrophoretic Displays, Grayscale and Color Rendition. *IDW*, AMD2/EP1-2, 243-246.
Ho, Andrew. (Nov. 2006) *Embedding e-Paper in Smart Cards, Pricing Labels &Indicators*. Presentation conducted at Smart Paper Conference Nov. 15-16, 2006, Atlanta, Ga, USA.
Ho, C., & Liang, R.C. (Dec. 2003). *Microcup® Electronic Paper by Roll-to-Roll Manufacturing Processes*. Presentation conducted at FEG, Nei-Li, Taiwan.
Ho, Candice. (Feb. 1, 2005) *Microcupt® Electronic Paper Device and Applicaiton*. Presentation conducted at USDC 4th Annual Flexible Display Conference 2005.
Hopper, M. A. et al, (1979) "An Electrophoretic Display, its Properties, Model and Addressing", IEEE Transactions on Electron Devices, 26(8): 1148-1152.
Hou, J., Chen, Y., Li, Y., Weng, X., Li, H. And Pereira, C. (May 2004). Reliability and Performance of Flexible Electrophoretic Displays by Roll-to-Roll Manufacturing Processes. *SID Digest*, 32.3, 1066-1069.
Kenny, et al., (1984), J. Am. Chem. Soc. 106, pp. 7404-7410.
Lee, H., & Liang, R.C. (Jun. 2003) *SiPix Microcup® Electronic Paper—An Introduction*. *Advanced Display*, Issue 37, 4-9 (in Chinese, English abstract attached).
Liang, R.C. (Feb. 2003) *Microcup(R) Electrophoretic and Liquid Crystal Displays by Roll-to-Roll Manufacturing Processes*. Presentation conducted at the Flexible Microelectronics & Displays Conference of U.S. Display Consortium, Phoenix, Arizona.

(Continued)

Primary Examiner—William C Choi
(74) Attorney, Agent, or Firm—Howrey LLP

(57) ABSTRACT

This invention relates to stable colorants of high extinction coefficient and high solubility or dispersibility for an electrophoretic, magnetophoretic or electromagnetophoretic display. More particularly, it relates to stable colorants for a microcup-based electrophoretic or electromagnetophoretic display the cells of which are filled with charged and/or magnetic particles dispersed in a halogenated, preferably a fluorinated, solvent. The use of the stable colorants allows the display to be of superior contrast ratio and longevity, and suitable for high-quality imagery applications.

25 Claims, No Drawings

OTHER PUBLICATIONS

Liang, R.C. (Apr. 2004). *Microcup Electronic Paper by Roll-to-Roll Manufacturing Process*. Presentation at the Flexible Displays & Electronics 2004 of Intertech, San Fransisco, California, USA.

Liang, R.C. (Oct. 2004) *Flexible and Roll-able Displays/Electronic Paper—A Technology Overview*. Paper presented at the METS 2004 Conference in Taipie, Taiwan.

Liang, R.C., & Tseng, S. (Feb. 2003). *Microcup(R) LCD, An New Type of Dispersed LCD by A Roll-to-Roll Manufacturing Process*. Paper presented at the IDMC, Taipei, Taiwan.

Liang, R.C., (Feb. 2005) *Flexible and Roll-able Displays/Electronic Paper—A Brief Technology Overview*. Flexible Display Forum, 2005, Taiwan.

Liang, R., Hou, J., & Zang, H.M. (Dec. 2002) Microcup Electrophoretic Displays by Roll-to-Roll Manufacturing Processes. *IDW*, EP2-2, 1337-1340.

Liang, R.C., Hou, J., Chung, J., Wang, X., Pereira, C., & Chen, Y. (May 2003). Microcup® Active and Passive Matrix Electrophoretic Displays by A Roll-to-Roll Manufacturing Processes. *SID Digest*, vol. 34, Issue 1, pp. 838-841, 20.1.

Liang, R.C., Hou, J., Zang, H.M., & Chung, J. (Feb. 2003). *Passive Matrix Microcup(R) Electrophoretic Displays*. Paper presented at the IDMC, Taipei, Taiwan.

Liang, R.C., Hou, J., Zang, H.M., Chung, J., & Tseng, S. (2003). Microcup® displays : Electronic Paper by Roll-to-Roll Manufacturing Processes. *Journal of the SID*, 11(4), 621-628.

Liang, R.C., Zang, H.M., Wang, X., Chung, J. & Lee, H., (Jun./Jul. 2004) << Format Flexible Microcup® Electronic Paper by Roll-to-Roll Manufacturing Process >>, Presentation conducted at the 14th FPD Manufacturing Technology Expo & Conference.

Studer, et al., (1997) "Fluorous Synthesis: Fluorous Protocols for the Ugi and Biginelli Multicomponent Condensations", Journal of Organic Chemisty, 62, pp. 2917-2924.

Wang, X., Kiluk, S., Chang, C., & Liang, R.C. (Feb. 2004). Microcup® Electronic Paper and the Converting Processes. *ASID*, 10.1.2-26, 396-399, Nanjing, China.

Wang, X., Kiluk, S., Chang, C., & Liang, R.C., (Jun. 2004) Microcup® Electronic Paper and the Converting Processes. *Advanced Display*, Issue 43, 48-52 (in Chinese, with English abstract).

Wang, X., Li, P., Sodhi, D., Xu, T. and Bruner, S. et al., (Feb. 2006) *Inkjet Fabrication of Multi-Color Microcup® Electrophorectic Display*. the Flexible Microelectronics & Displays Conference of U.S. Display Consortium.

Wang, X., Zang, HM., and Li, P. (Jun. 2006) Roll-to-Roll Manufacturing Process for Full Color Electrophoretic film. *SID Digest*, 00, pp. 1587-1589.

Zang, H.M, Hwang, J.J., Gu, H., Hou, J., Weng, X., Chen, Y., et al. (Jan. 2004). Threshold and Grayscale Stability of Microcup® Electronic Paper. *Proceeding of SPIE-IS&T Electronic Imaging, SPIE* vol. 5289, 102-108.

Zang, H.M. & Hou, Jack (Feb. 2005) *Flexible Microcup® EPD by RTR Process*. Presentation conducted at 2nd Annual Paper-Like Displays Conference, Feb. 9-11, 2005, St. Pete Beach, Florida.

Zang, H.M. (Oct. 2003). *Microcup® Electronic Paper by Roll-to-Roll Manufacturing Processes*. Presentation conducted at the Advisory Board Meeting, Bowling Green State University, Ohio, USA.

Zang, H.M. (Feb. 2004). *Microcup Electronic Paper*. Presentation conducted at the Displays & Microelectronics Conference of U.S. Display Consortium, Phoenix, Arizona, USA.

Zang, H.M., & Liang, R.C. (2003) Microcup Electronic Paper by Roll-to-Roll Manufacturing Processes. *The Spectrum*, 16(2), 16-21.

Zang, HM., (Feb. 2007) *Developms in Microcup® Flexible Displays*. Presentation conducted at the 6th Annual Flexible Display and Microelectronics Conferencee, Phoenix, AZ Feb. 6-8.

Zang, HM., (Sep. 2006) *Monochrome and Area Color Microcup® EPDs by Roll-to-Roll Manufacturing Process*. Presentation conducted at the Forth Organic Electronics Conference and Exhibition (OEC-06), Sep. 25-27, 2006, Frankfurt, Germany.

Zang, HM., Wang, W., Sun, C., Gu, H., and Chen, Y. (May 2006) Monochrome and Area Color Microcup® EPDs by Roll-to-Roll Manufacturing Processes. *ICIS ' 06 International Congress of Imaging Science Final Program and Proceedings*, pp. 362-365.

\* cited by examiner

FLUORINATED SILICON PHTHALOCYANINES AND NAPHTHALOCYANINES FOR ELECTROPHORETIC DISPLAY

This application is a divisional application of U.S. application Ser. No. 10/439,428, filed May 15, 2003 now abandoned; which claims the benefit of U.S. Provisional Application No. 60/381,263, filed May 17, 2002. Both applications are incorporated herein by reference in their entirety.

BACKGROUND

1. Field of the Invention

This invention relates to stable colorants of high extinction coefficient and high solubility or dispersibility for an electrophoretic, magnetophoretic or electromagnetophoretic display. More particularly, it relates to stable colorants for a microcup-based electrophoretic, magnetophoretic or electromagnetophoretic display the cells of which are filled with charged and/or magnetic particles dispersed in a halogenated, preferably a fluorinated, solvent. The use of the stable colorants allows the display to be of superior contrast ratio and longevity, and suitable for high-quality imagery applications.

2. Brief Description of Related Art

The electrophoretic display (EPD) is a non-emissive device based on the electrophoresis phenomenon influencing the migration of charged pigment particles in a solvent, preferably a colored dielectric solvent. This type of display was first proposed in 1969. An EPD typically comprises a pair of opposed, spaced-apart plate-like electrodes, with spacers predetermining a certain distance between the electrodes. At least one of the electrodes, typically on the viewing side, is transparent. For the passive type of EPDs, row and column electrodes on the top (the viewing side) and bottom plates respectively, are needed to drive the displays. In contrast, an array of thin film transistors (TFTs) on the bottom plate and a common, non-patterned transparent conductor plate on the top viewing substrate are required for the active type EPDs.

An electrophoretic fluid composed of a colored dielectric solvent with charged pigment particles dispersed therein is enclosed between the two electrodes. When a voltage difference is imposed between the two electrodes, the pigment particles migrate by attraction to the plate of polarity opposite that of the pigment particles. Thus, the color showing at the transparent plate, determined by selectively charging the plates, can be either the color of the solvent or the color of the pigment particles. Reversal of plate polarity will cause the particles to migrate back to the opposite plate, thereby reversing the color. Intermediate color density (or shades of gray) due to intermediate pigment density at the transparent plate may be obtained by controlling the plate charge through a range of voltages or pulsing time.

EPDs of different pixel or cell structures have been reported previously, for example, the partition-type EPD (M. A. Hopper and V. Novotny, IEEE Trans. Electr. Dev., Vol. ED 26, No. 8, pp. 1148-1152 (1979)) and the microencapsulated EPD (U.S. Pat. Nos. 5,961,804 and 5,930,026).

An improved EPD technology was recently disclosed in co-pending applications, U.S. Pat. No. 6,930,818 (corresponding to WO 01/67170), U.S. Pat. No. 6,672,921, (corresponding to WO 02/01281) and U.S. Pat. No. 6,933,098, (corresponding to WO 02/65215), all of which are incorporated herein by reference. The improved EPD comprises isolated cells formed from microcups and filled with charged particles dispersed in a dielectric solvent. The filled cells are individually sealed with a polymeric sealing layer, preferably formed from a composition comprising a material selected from a group consisting of thermoplastics, thermosets and precursors thereof.

Other types of displays, namely magnetophoretic displays (MPDs) and electromagnetophoretic displays (EMPDs), are disclosed in U.S. Pat. Nos. 6,927,892 and 6,914,713, filed on Apr. 23, 2002, the contents of both are incorporated herein by reference in their entirety.

The magnetophoretic display generally comprises display cells sandwiched between two layers of substrate and filled with a magnetophoretic dispersion wherein the pigment particles are magnetic but not charged. The display is driven by a magnetic field. At least the substrate layer on the viewing side is transparent.

In the electromagnetophoretic display, the display cells sandwiched between two substrate layers are filled with an electromagnetophoretic fluid wherein the pigment particles are both charged and magnetic. One of the substrate layers, preferably on the non-viewing side, is coated with a conductive layer facing the filled display cells. The display is driven by a combination of electric and magnetic fields. The substrate layer on the viewing side is transparent.

For all types of displays, the dispersion contained within the display cells is undoubtedly one of the most crucial parts of the device. The dispersion, as stated earlier, usually is composed of pigment particles dispersed in a colored dielectric solvent or solvent mixture. The composition of the dispersion determines, to a large extent, the longevity, contrast ratio, switching rate, response waveform and bistability of the device. In an ideal dispersion, the dispersed pigment particles remain separate and do not aggregate or flocculate under all operating conditions. Furthermore, all components in the dispersion must be chemically and electrochemically stable and compatible not only with each other but also with the other materials present in a display, such as the electrodes and sealing and substrate materials.

The dispersing medium may be colored by dissolving or dispersing a dye or colorant in the dielectric solvent or solvent mixture.

Halogenated solvents of high specific gravity have been widely used in EPD applications, particularly in those involving an inorganic pigment, such as $TiO_2$, as the charged whitening or coloring particles. The halogenated solvents of high specific gravity are very useful in reducing the rate of sedimentation of the pigment particles in the solvent. Fluorinated solvents are among the most preferred because they are chemically stable and environmentally friendly.

However, most dyes or pigments are not soluble in fluorinated solvents, particularly not in high boiling-point perfluorinated solvents. For example, phthalocyanines are highly desirable colorants due to their high extinction coefficients, narrow absorption bands and chemical stability; but they are normally insoluble in most solvents, and are particularly insoluble in fluorinated solvents. Therefore, displays based on fluorinated dielectric solvents colored by this type of dyes typically show poor shelf-life stability, contrast ratio and switching performance.

Certain soluble fluorinated copper phthalocyanine dyes are disclosed in U.S. Pat. No. 3,281,426 (1966). The process for the preparation of these dyes involves heating a mixture of an aromatic starting compound and a perfluoroalkyliodide at a temperature in the range of from 200° C. to 350° C. The reaction is performed in an autoclave or a pressure ampoule due to the pressure developed. This synthesis involves complicated reaction conditions (e.g., high pressure and temperature) and long reaction time and has a low yield. Other phthalocyanine derivatives (U.S. Pat. Nos. 6,043,355 and 5,932, 721) show improved solubility in various organic solvents or even in water, but not in highly fluorinated solvents.

Thus, there is a need for stable dyes or colorants that exhibit high solubility or dispersibility in halogenated, particularly fluorinated, dielectric solvents for use in display applications. The dyes or colorants should also have a high extinction coefficient, narrow adsorption bands and chemical or electrochemical stability, and can be manufactured in high yields at low cost.

SUMMARY OF THE INVENTION

The first aspect of the present invention is directed to a group of novel fluorinated silicon phthalocyanine and naphthalocyanine dyes which comprise a fluorine content of at least 20% by weight, preferably at least 30% by weight and more preferably at least 50% by weight.

A second aspect of the invention is directed to a display composition which comprises one or more fluorinated silicon phthalocyanine or naphthalocyanine dye of the first aspect of the invention as a colorant dissolved or dispersed in a dielectric solvent or solvent mixture, particularly in a fluorinated dielectric solvent or solvent mixture in which pigment particles are suspended.

A third aspect of the invention is directed to a display composition of the second aspect of the invention further comprising a non-silicon phthalocyanine or naphthalocyanine dye, preferably a fluorinated metal phthalocyanine dye in addition to the dyes of the first aspect of the invention.

A fourth aspect of the invention is directed to an electrophoretic, magnetophoretic or electromagnetophoretic display the cells of which are filled with a display composition of the second or third aspect of the invention.

A fifth aspect of the invention is directed to a microcup-based display which comprises sealed display cells filled with a display composition of the second or third aspect of the invention.

DETAILED DESCRIPTION OF THE INVENTION

I. Definitions

Unless defined otherwise in this specification, all technical terms are used herein according to their conventional definitions as they are commonly used and understood by those of ordinary skill in the art.

The term "alkyl" is broader than the customary chemical definition and refers to a linear, branched or cyclic hydrocarbon radical. Unless otherwise indicated, the alkyl group may have 1 to 20, preferably 1 to 12 carbon atoms. For example, it may be methyl, ethyl, cyclohexyl, octyl, n-decyl or the like which is optionally unsaturated, such as ethenyl, 3-hexenyl or the like.

The term "heteroalkyl" refers an "alkyl" as defined above in which one or more carbon atoms are replaced by O, S or N.

The term "alkoxy" refers to the group —O—R wherein R is an alkyl as defined above. The term "heteroalkoxy" refers to the group —O—R wherein R is a heteroalkyl as defined above.

The term "aryl", as in "aryl", "arylalkyl" or "alkylaryl", refers to an organic radical derived from an aromatic hydrocarbon having 6 to 18 carbon atoms including, but not limited to, phenyl, naphthyl, anthracenyl and the like.

The term "heteroaryl" refers to an organic radical derived from an aromatic hydrocarbon in which one or more of the ring carbon atoms are replaced by O, S or N, such as pyridyl, thienyl, furanyl or pyrrolyl.

The term "halogenated" or "fluorinated" refers to a moiety which is partially or completely substituted with halogen atoms or fluorine atoms, respectively.

II. Fluorinated Silicon Phthalocyanine and Naphthalocyanine Dyes

The novel fluorinated silicon phthalocyanine (I) and naphthalocyanine (II) dyes of the present invention may be expressed by the following formulas:

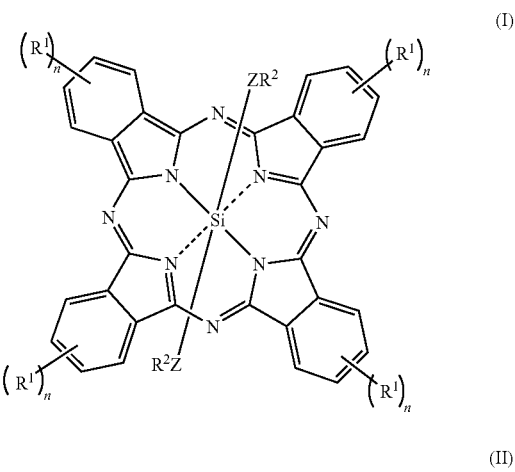

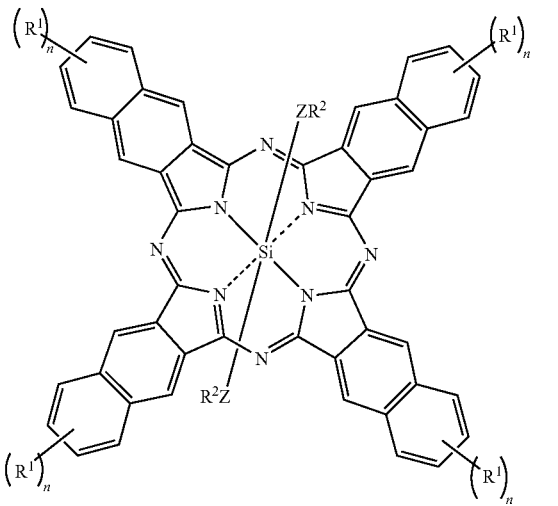

wherein:

each n is individually 0-4 for silicon phthalocyanine (I) or 0-6 for silicon naphthalocyanine (II);

$R^1$ is independently $R_f$-A- (wherein $R_f$ is as defined below and A is a single bond, —$CH_2$—, —$CH_2CH_2O$— or —CO—), alkyl, heteroalkyl, aryl, heteroaryl, heteroalkylaryl, alkylheteroaryl, heteroarylalkyl aryl-heteroalkyl, R'O—, R'S—, R'R"N—, R'CO—, R'OCO—, R'COO—, R'CONR"—, R'R"NCO—, R'NHCONR"—, $R'SO_2NR"$— or $R'R"NSO_2$— (in which R' and R" are independently hydrogen, $R_f$ (as defined below), alkyl, heteroalkyl, aryl, heteroaryl, heteroarylalkyl, aryl-heteroalkyl, heteroalkyaryl or alkyl-heteroaryl) or halogenated, particularly fluorinated derivatives thereof;

Z is O or NR' wherein $R^1$ is defined as above;

$R^2$ is hydrogen, $R_f$—B— (wherein $R_f$ is as defined below and B is a single bond, —$CH_2$— or —$CH_2CH_2$—), alkyl, heteroalkyl or halogenated, particularly fluorinated derivatives thereof, or —$SiR^3R^4R^5$ wherein $R^3$, $R^4$, and $R^5$ are independently an alkyl or fluoroalkyl group of 1 to 20 carbon atoms or alkoxy or fluoroalkoxy of 2 to 40 carbon atoms; and $R_f$ is a low molecular weight (100-100,000) fluorinated polymeric or oligomeric moiety prepared from one or more types of fluorinated monomers.

Useful fluorinated monomers may include, but are not limited to, epoxide, hydrofuran, cyclolactone, cyclolactam, acrylate, methacrylate, styrene, vinylether and vinylalkane.

The substituents, $R^1$, $R^2$, $R^3$, $R^4$, $R^5$, $R_f$, and n are so selected that the total fluorine content of the silicon phthalocyanine dye is at least 20%, preferably at least 30% and more preferably at least 50%, by weight of the dye molecule.

It will be recognized that when the preparation of the compounds involves the reaction of a formed phthalocyanine/naphthalocyanine or silicon phthalocyanine/naphthalocyanine with a reagent that inserts $R^1$ groups, the resulting product may be a mixture of compounds having different degrees of $R^1$ substitution on the phthalocyanine/naphthalocyanine rings, so that n, when not 0, may be different on each of the phenyl or naphthyl moiety within a compound; and it will also be recognized that substitution may occur at different positions on the different phenyl/naphthyl rings of the phthalocyanine/naphthalocyanine; and all such compounds are within the scope of the present invention. In addition, when n is not 0, not all $R^1$ groups need be the same, either within the compound as a whole or even on a particular phenyl or naphthyl moiety within a compound.

Preferred Embodiments

In the compounds of Formula (I) and (II), n is preferably 0-2, preferably 0-1. For example, n may be 0.

Each $R^1$ is independently an alkyl or alkoxy group, preferably a halogenated alkyl or alkoxy group, more preferably a fluorinated alkyl or alkoxy group. Especially preferred $R^1$ groups are fluorinated, especially completely fluorinated alkyl of 1 to 12 carbon atoms, more preferably 6 to 10 carbon atoms.

The substituent, Z, is preferably oxygen.

The substituent, $R^2$, is preferably hydrogen, $R_f$—$CH_2$—, alkyl and fluoroalkyl as defined above or —$SiR^3R^4R^5$ wherein $R^3$, $R^4$ and $R^5$ are independently an alkyl group such as methyl, a fluorinated alkyl chain of 6 to 12 carbon atoms or a fluorinated alkoxy of 6 to 18 carbon atoms. In one embodiment, $R^3$, $R^4$ and $R^5$ may be independently an alkyl, a fluorinated alkyl such as —$(CH_2)_2(CF_2)_5CF_3$ or $(CH_2)_2(CF_2)_7CF_3$ or a fluorinated alkoxy such as —$OCH_2(CF_2)_{12}CF_3$ or $CH_2(CF_2)_6CF_3$.

$R_f$ is as defined above and is preferably a low molecular weight (200-20,000, more preferably 400-10,000) fluorinated polymer or oligomer. Examples of $R_f$ may include perfluoropolyether and hydrofluoropolyether derived from the monomer, perfluoropropylene oxide, or from oligomers such as Krytox® K-fluids (trifluorohomopolymer) from Dupont and HT or ZT series from Ausimont; and poly(chlorotrifluoroethylene) derived from the monomer, chlorotrifluoroethylene, or from oligomers such as Halocarbon Oils from Halocarbon Product Corp. (River Edge, N.J.).

In one embodiment, $R_f$ is a monovalent radical derived from a halogenated, especially a fluorinated, optionally substituted, alkylene or alkylene oxide homopolymer or copolymer having a molecular weight between 200 and 20,000.

In another embodiment, $R_f$ may be expressed by the following formula:

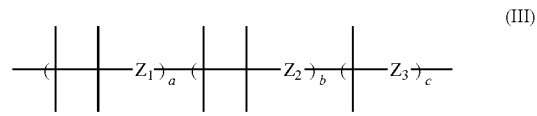

(III)

wherein the open substituent positions (not designated) on the main chain of the formula can be the same or different and may independently be selected from a group consisting of hydrogen, halogen (especially fluorine), alkyl, aryl, alkylaryl, fluorinated alkyl, fluorinated aryl, fluorinated alkylaryl, —$OR^6$, $OCOR^6$, —$COOR^6$, —$CONR^6R^7$ (wherein $R^6$ and $R^7$ are independently hydrogen, alkyl, aryl, alkylaryl, fluorinated alkyl, especially perfluoroalkyl, fluorinated aryl, especially perfluorinated aryl) and substituted derivatives thereof;

$Z_1$, $Z_2$, and $Z_3$ are independently oxygen or absent; and a, b, and c are the weight fractions of the corresponding repeating units and are independently in the range of 0-1 with their sum equal to 1.

In one embodiment, the open substituent positions on the main chain of Formula (III) may be independently fluorine or fluoroalkyl, such as —$CF(CF_3)[OCF_2CF(CF_3)]_nF$ or the like When $R^1$ is Rf-A-, A is preferably —$CH_2$—, —$CH_2CH_2O$— or —CO—. When $R^2$ is Rf-B—, B is preferably —$CH_2$—.

The dyes of the present invention are highly soluble or dispersible in fluorinated solvents, and exhibit high extinction coefficients and good thermal and light fastness. Therefore, they are particularly suitable for use as colorants in displays. They may also be used as colorants for color filters, coatings, adhesives and lubricants.

III. Synthesis of Fluorinated Silicon Phthalocyanine Dyes

The compounds of the present invention may be prepared according to conventional methods. Most of the compounds in the present invention may be synthesized according to the following reaction scheme:

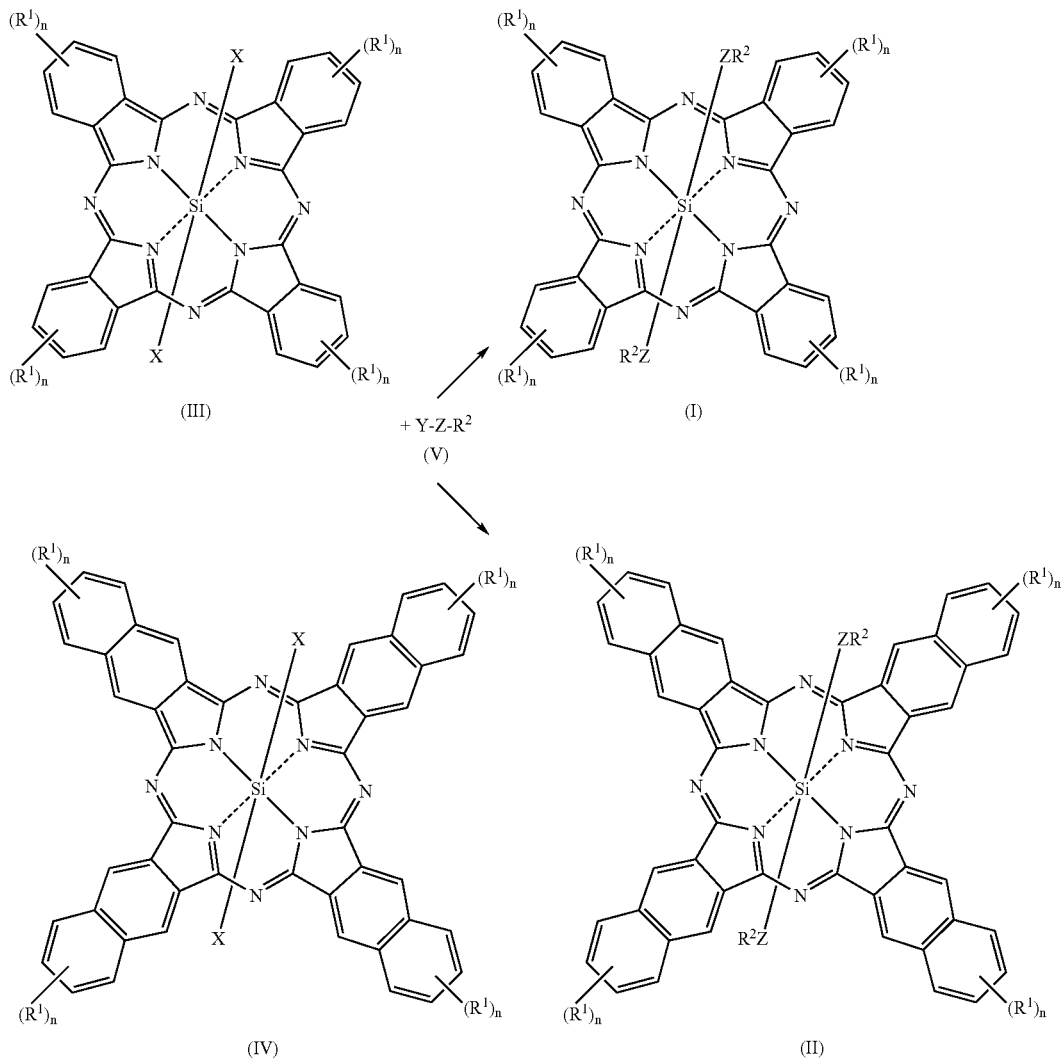

wherein n, $R^1$, $R^2$ and Z are as defined above;
X is halogen or hydroxy; and Y is hydrogen or an alkali metal such as sodium, potassium or lithium.

The compounds of Formulas III and IV are commercially available (for example, from Aldrich) or may be prepared by commercially available compounds. The X substituent in Formula III and Formula IV is preferably chlorine or hydroxy. The compound of Formula (V) wherein Y is hydrogen can be converted to an alkali salt by, for example, refluxing with an alkali metal in anhydrous ether.

A compound of Formula I or II wherein Z is oxygen and $R^2$ is $-SiR^3R^4R^5$ may be prepared by reacting a compound of Formula III or IV wherein X is hydroxy with $SiR^3R^4R^5Cl$ or $SiR^3R^4R^5Br$. The Si reagents are commercially available (for example, from Gelest) or may be prepared according to Example 3A below. In general, these reagents are prepared according to methods described in J. Org. Chem., 1997, 62, 2917-2924.

Alternatively, the preparation of a compound of Formula I or Formula II wherein Z is oxygen and $R^2$ is $-SiR^3R^4R^5$ may be carried out in steps. For example, a compound of Formula III wherein X is hydroxy may be first reacted with $SiR^3Cl_3$; the intermediate compound thus obtained is then reacted with a compound of $R^4OH$ to form a compound of Formula I wherein $R^2$ is $-SiR^3R^4R^5$ in which $R^3$ and $R^4$ are as defined above and $R^5$ is the same as $R^4$. The reaction conditions of the two step process are exemplified in Example 2 below.

The substituent, $R^1$, on the ring structure may be added on by conventional methods as demonstrated in Example 5 below.

IV. Display Compositions Containing the Fluorinated Silicon Phthalocyanine or Naphthalocyanine Dye The term "display composition" refers to an electrophoretic, magnetophoretic or electromagnetophoretic dispersion.

The dyes of the present invention are highly soluble in fluorinated solvents, particularly perfluorinated solvents and have high extinction coefficients in the 500-700 nm region. A solvent having low vapor pressure, low viscosity and a dielectric constant in the range of about 1.5 to about 30, more preferably about 2 to about 10, are generally needed as the dielectric solvent of the electrophoretic fluid. Examples of suitable fluorinated solvents for EPD applications include, but are not limited to, fluorinated and perfluorinated solvents such as perfluoroalkanes or perfluorocycloalkanes (e.g., perfluorodecalin), perfluoroarylalkanes (e.g., perfluorotoluene or perfluoroxylene), perfluoro-tert-amines, perfluoropolyethers such as those from Galden/Fomblin and perfluoropolyethers HT series, and hydrofluoropolyethers (ZT series) from Ausimont, FC-43 (heptacosafluorotributylamine), FC-70 (perfluorotri-n-pentylamine), PF-5060 or PF-5060DL (perfluorohexane) from 3M Company (St. Paul, Minn.), low molecular weight (preferably less than 50,000, more preferably less than 20,000) polymers or oligomers such as poly (perfluoropropylene oxide) from TCI America (Portland, Oreg.), poly(chlorotrifluoroethylene) such as Halocarbon Oils from Halocarbon Product Corp. (River Edge, N.J.), Krytox® K-fluids (trifluorohomopolymer) from Dupont, and Demnum lubricating oils from Daikin Industries. Perfluoropolyethers and hydrofluoropolyethers such as Ausimont HT-170, HT-200, HT-230, ZT-180 and Dupont trifluoro(trifluoromethyl)-oxirane homopolymers (such as K-6 and K-7 fluids) are particularly useful.

The display composition may comprise one or more fluorinated silicon phthalocyanine dye and fluorinated naphthalocyanine dye as a colorant in a dielectric solvent, especially a fluorinated dielectric solvent. The composition may further comprise a fluorinated non-silicon phthalocyanine or naphthalocyanine dye, particularly a fluorinated metal phthalocyanine or naphthalocyanine dye to enhance the color saturation. The metal may be Cu, Mg or Zn. These metal phthalocyanine dyes are available commercially or may be synthesized according to U.S. Pat. No. 3,281,426.

The use of a mixture of a dye of the present invention and a Cu phthalocyanine dye is preferable because the colorant mixture increases the low temperature (particularly subzero C) latitude of the display over that of a comparable display using only the fluorinated Cu phthalocyanine dye. Without being limited by theory, it is considered that this may be due to the higher solubility of the present dye in the electrophoretic fluid. The solubility of the present dye in a perfluorinated solvent such as HT-200 is about 3-5 wt % whereas the solubility of the Cu dye in the same solvent is only about 1-1.5 wt %. To achieve a high contrast ratio, a concentration of about 1.5 wt % of the Cu dye is needed. However, due to its low solubility, the Cu dye inevitably will precipitate out at low temperature (subzero) and as a result, the switching performance of the display deteriorates dramatically. By mixing a Si dye of the present invention with the Cu dye, a high contrast ratio can be achieved without tradeoff in the low temperature latitude. It also broadens the visible spectrum and increases the color saturation in a monochrome display. The ratio of the Si dye to the Cu dye in the mixture may range from 1/10 to 10/1, preferably 1/5 to 5/1 and more preferably 1/3 to 3/1.

The charged pigment particles visually contrast with the fluorinated solvent in which the particles are suspended. The primary pigment particles may be organic or inorganic pigments, such as $TiO_2$, diarylide yellow, diarylide AAOT yellow, and quinacridone, azo, rhodamine, perylene pigment series from Sun Chemical, Hansa yellow G particles from Kanto Chemical and Carbon Lampblack from Fisher. The pigment particles may be prepared by any of the well-known methods including grinding, milling, attriting, microfluidizing and ultrasonic techniques. For example, pigment particles in the form of a fine powder are added to the suspending solvent and the resulting mixture is ball milled or attrited for several hours to break up the highly agglomerated dry pigment powder into primary particles. Particle size of the pigment particles is preferably in the range of 0.01-10 microns, more preferably in the range of 0.05-3 microns. These particles should have acceptable optical characteristics, should not be swollen or softened by the dielectric solvent and should be chemically stable. The resulting dispersion must also be stable against sedimentation, creaming or flocculation under normal operating conditions.

In order for the display composition to achieve high hiding power or light scattering efficiency, high dispersion stability, low rate of sedimentation or creaming and high mobility even with a high solid content and under a wide range of applied voltages, the pigment particles are preferably microencapsulated or coated with a polymer matrix of low specific gravity. Microencapsulation of the pigment particles may be accomplished chemically or physically. Typical microencapsulation processes include interfacial polymerization/crosslinking, in-situ polymerization/crosslinking, phase separation, simple or complex coacervation, electrostatic coating, spray drying, fluidized bed coating and solvent evaporation. Improved processes of making density-matched pigment microcapsules of high mobility involving the use of reactive protective colloids and charge controlling agents are disclosed in U.S. Ser. No. 60/345,936, filed on Jan. 3, 2002, U.S. Ser. No. 60/345,934 filed on Jan. 3, 2002, U.S. Ser. No. 10/335,210 filed on Dec. 31, 2002 and U.S. Ser. No. 10/335,051 filed on Dec. 31, 2002, all of which are incorporated herein by reference.

The resulting display composition may then be filled into the display cells and sealed.

V. Electrophoretic, Magnetophoretic or Electromagnetophoretic Display of the Present Invention The display cells may be the conventional partition type cells (as disclosed in M. A. Hopper and V. Novotny, IEEE Trans. Electr. Dev., Vol. ED 26, No. 8, pp. 1148-1152 (1979)), the microcapsule type cells (as disclosed in U.S. Pat. Nos. 5,961,804 and 5,930,026) and the display cells prepared from the microcup technology as disclosed in co-pending applications, U.S. Ser. No. 09/518,488, filed on Mar. 3, 2000 (corresponding to WO 01/67170 published on Sep. 13, 2001), U.S. Ser. No. 09/759,212, filed on Jan. 11, 2001 (corresponding to WO 02/56097 published on Jul. 18, 2002), U.S. Ser. No. 09/606,654, filed on Jun. 28, 2000 (corresponding to WO 02/01281 published on Jan. 3, 2002) and U.S. Ser. No. 09/784,972, filed on Feb. 15, 2001 (corresponding to WO 02/65215 published on Aug. 22, 2002), all of which are incorporated herein by reference. The improved microcup-based display comprises isolated cells formed from microcups of well-defined shape, size and aspect ratio and filled with charged particles dispersed in a dielectric solvent or solvent mixture, preferably a halogenated solvent, particularly a fluorinated solvent. The filled cells are individually sealed with a polymeric sealing layer, preferably formed from a composition comprising a material selected from a group consisting of thermoplastics, thermosets and precursors thereof.

EXAMPLES

Preparation 1

Preparation of $R_f$-Amine Oligomers for Microencapsulation

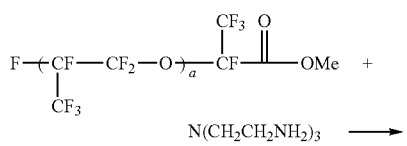

$N(CH_2CH_2NH_2)_3$ ⟶

-continued

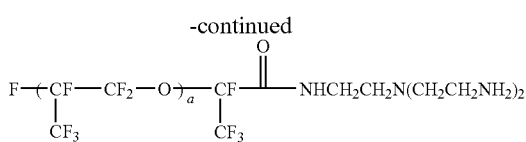

17.8 Grams of Krytox® methyl ester (MW=~1780, a=about 10, from DuPont) was dissolved in a mixture of 12 g of 1,1,2-trichlorotrifluoroethane (Aldrich) and 1.5 g of α,α, α-trifluorotoluene (Aldrich). The resulting solution was added drop by drop into a solution containing 7.3 g of tris(2-aminoethyl)amine (MW=146, from Aldrich) in 25 g of α,α, α-trifluorotoluene and 30 g of 1,1,2-trichlorotrifluoroethene, over 2 hours with stirring at room temperature. The mixture was then stirred for another 8 hours to allow the reaction to complete. The IR spectrum of the product clearly indicated the disappearance of the C=O vibration for the methyl ester at 1780 cm$^{-1}$ and the appearance of the C=O vibration for the amide product at 1695 cm$^{-1}$. The solvents were removed by rotary evaporation followed by vacuum stripping at 10° C. for 4-6 hours (1 Torr). The crude product was then dissolved in 50 ml of PFS-2 solvent (low molecular weight perfluoropolyether from Ausimont) and extracted three times with 20 ml of ethyl acetate; then dried to yield 17 g of purified product ($R_f$-amine1900) which showed excellent solubility in HT200. $R_f$-amine-650 (a=about 3) was also synthesized according to the same procedure Preparation 2

Preparation of Density Matched $TiO_2$ Microcapsules 5.9 Grams of $TiO_2$ R900 (DuPont) was added to a solution consisting of 3.77 g of MEK, 4.31 g of N3400 aliphatic polyisocyanate (Bayer AG) and 0.77 g of 1-[N,N-bis(2-hydroxyethyl)amino]-2-propanol (Aldrich). The resulting slurry was homogenized for 1 minute at 5-10° C.; 0.01 g of dibutyltin dilaurate (Aldrich) was added and homogenized for an additional minute at 5-10° C.; and finally a solution containing 20 g of HT-200 and 0.47 g of $R_f$-amine1900 (from Preparation 1) was added and homogenized again for 3 minutes at room temperature.

The slurry prepared above was emulsified slowly at room temperature by a homogenizer into a mixture of 31 g of HT-200 and 2.28 g of Rf-amine-650 (from Preparation 1). The resulting microcapsule dispersion was kept stirring under low shear by a mechanical stirrer at 35° C. for 30 minutes and at 80° C. for 3 hours to remove MEK and post cure the microcapsules. The microcapsule dispersion showed a narrow particle size distribution ranging from 0.5-3.5 microns. The microcapsules were separated by centrifuge, rinsed with an excess of HT-200 and finally re-dispersed in HT-200.

Example 1

Synthesis and Evaluation of Fluorinated Silicon Phthalocyanine Compound (1)

As shown in Scheme 1 below, the 2 step, 1 pot procedure involves conversion of a highly fluorinated ether alcohol (Krytox™ from DuPont) to its sodium salt, followed by, without isolation, reaction with silicon phthalocyanine dichloride (Aldrich).

The Structure of Compound (1)

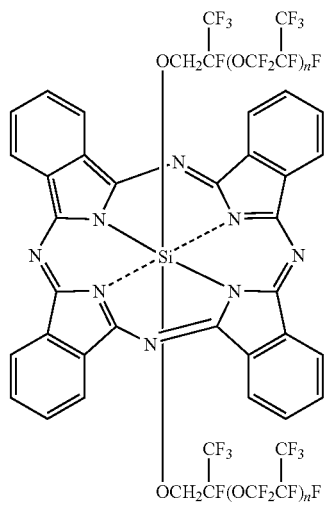

Scheme 1: The synthetic route of Compound (1)

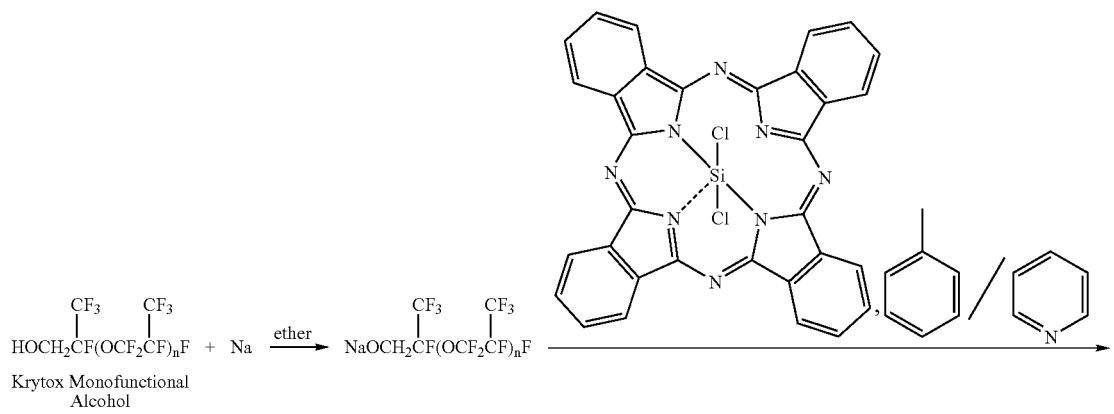

Compound (1)

A mixture of Krytox™ monofunctional alcohol (M.W. 1571, 6.51 g, 4.15 mmol, DuPont), sodium lump (0.14 g, 6.09 mmol) and anhydrous ether (20 mL) was refluxed for 23 hours under Ar atmosphere. The resulting mixture was added to a suspension of silicon phthalocyanine dichloride [dichloro (29H,3H-phthalocyaninato)silicon, SiPcCl$_2$] (1.00 g, 1.64 mmol, Aldrich), toluene (80 mL) and pyridine (20 mL), where the toluene and pyridine each had been dried by distillation (~10 mL of distillate) via pipette (without adding unreacted sodium pieces). The resulting mixture was distilled slowly over 24 hours (~40 mL distillate) via a Dean-Stark trap for water removal. The blue suspension obtained was mixed with Al$_2$O$_3$ (activity grade 1, neutral, 44 g, Fisher Scientific) and evaporated to dryness by rotary evaporation (60° C.) under pump vacuum (~5 Torr). The resulting blue solid was added to an extraction thimble and extracted with ether (300 mL, Fisher Scientific)) by Soxhlet extraction for 21 hours. The resulting dark blue extract was evaporated to dryness by rotary evaporation (60° C.) under pump vacuum (~5 Torr). A dark blue sticky solid, Compound (1), was obtained (5.66 g, 92%).

An EPD fluid containing 2 wt % of Compound (1) and 6 wt % solid of the TiO2 microcapsules (from Preparation 2) in HT-200 was prepared and filled between two ITO glass plates using PET films (35 microns thick, from DuPont, Hopewell, Va.) as the spacers. A contrast ratio of 11 was measured using a Spectrolino GretagMacbeth™ at a switching voltage of 80 V.

Example 2

Synthesis and Evaluation of Fluorinated Silicon Phthalocyanine Compound (2)

The Structure of Compound (2)

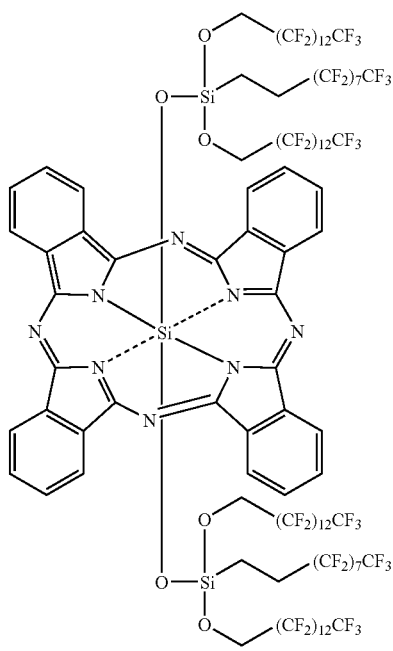

Scheme 2: The synthetic route of Compound (2)

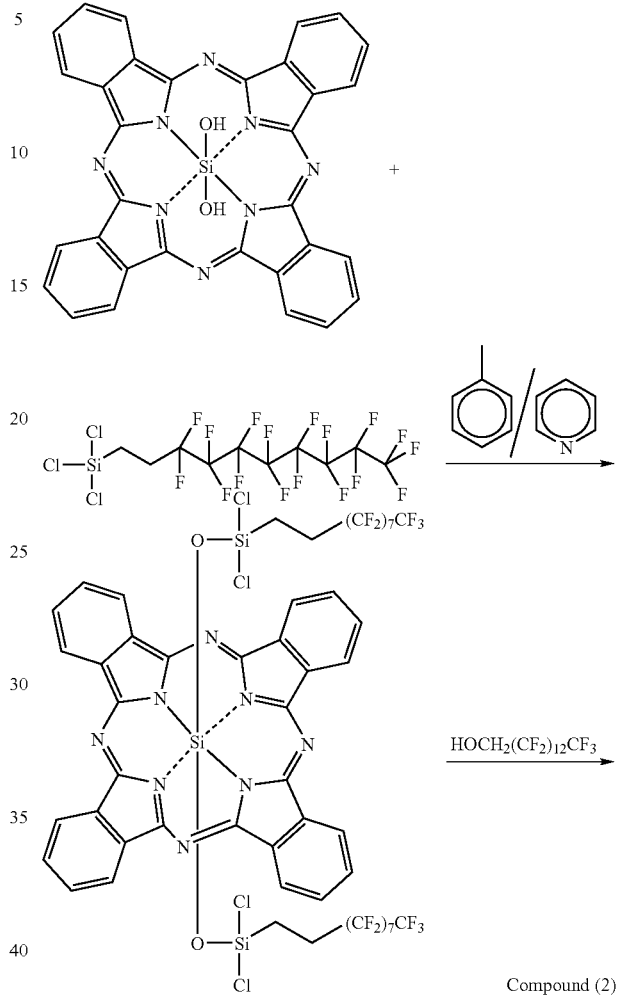

As shown in Scheme 2, a mixture of (heptadecafluoro-1,1,2,2-tetrahydrodecyl)trichlorosilane (1.30 mL, Gelest) and a suspension of SiPc(OH)$_2$ (0.51 g, 0.87 mmol, Aldrich) in toluene (80 mL) and pyridine (20 mL), where the toluene and pyridine each had been dried by distillation (~15 mL of distillate), was refluxed for 14 hours. 1H,1H-Perfluoro-1-tetradecanol (6.21 g, 0.89 mmol, Lancaster) was added to the resulting solution after cooling to room temperature and the mixture was slowly distilled for 23 hours (~15 mL distillate). The blue solution obtained was mixed with Al$_2$O$_3$ (20 g, activity grade I, neutral, Fisher Scientific) and evaporated to dryness by rotary evaporation (60° C.) under pump vacuum (~5 Torr). The resulting blue solid was added into a thimble and was extracted with PFS-2™ (150 mL, Ausimont) by Soxhlet extraction for 6 hours. The resulting dark blue extract was evaporated to dryness by rotary evaporation (60° C.) under pump vacuum (~5 Torr). A dark blue sticky solid, Compound (2), was obtained (3.44 g, yield 91%).

An EPD fluid containing 2 wt % of Compound (2) and 6 wt % solid of the TiO$_2$ microcapsules (from Preparation 2) in HT200 was prepared and evaluated as in Example 1. A contrast ratio of 15 was observed at a switching voltage of 80 V.

Example 3

Synthesis and Evaluation of Fluorinated Silicon Phthalocyanine Compound (3)

The structure of Compound (3)

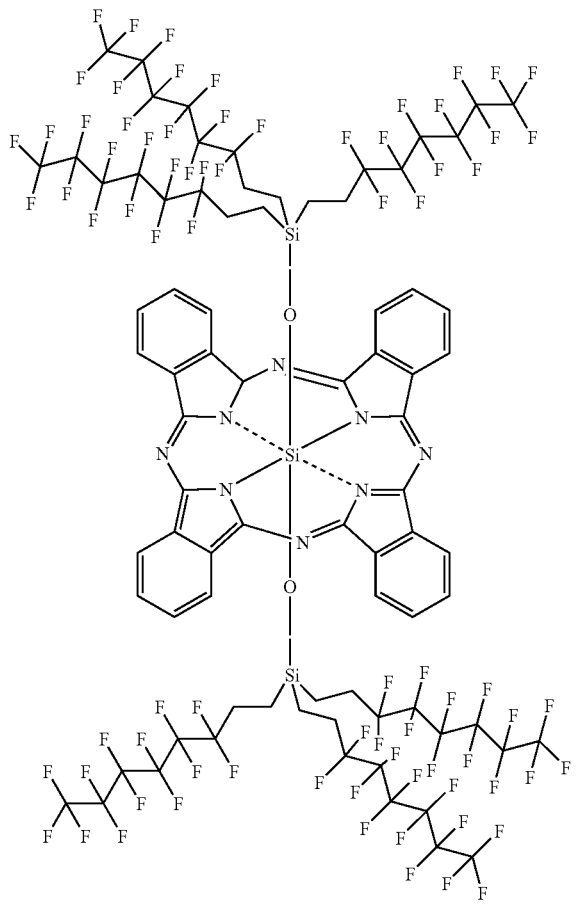

Scheme 3: The synthetic route of Compound (3)

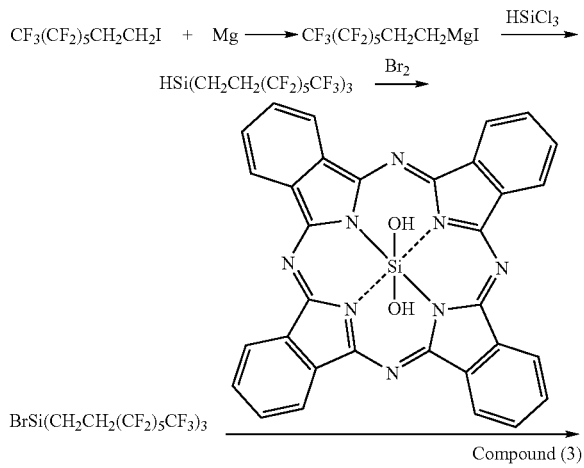

A. Synthesis of Bromosilane (A): BrSi(CH$_2$CH$_2$CF$_2$CF$_2$CF$_2$CF$_2$CF$_2$CF$_3$)$_3$ This procedure was modified from the synthesis described in *J. Org. Chem.*, 1997, 62, 2917-2924. A mixture of magnesium turnings (1.00 g, 40.9 mmol, Aldrich), 2 crystals of iodine (Fisher Scientific) and dry ether (10.0 mL, Fisher Scientific) was refluxed for 40 min, then cooled to room temperature. 1-Iodo-1H,1H,2H,2H-perfluorooctane (12.2 g, 25.6 mmol, Lancaster) in a dry ether solution (50 mL, Fisher Scientific) was added dropwise into the above mixture over 30 minutes. The mixture was refluxed for 15 hours. Trichlorosilane (0.80 mL, 7.98 mmol, Aldrich) was added into the resulting suspension after cooling and the suspension was refluxed for another 21 hours. The suspension obtained was filtered in order to remove unreacted magnesium turning. The filtrate was combined with a saturated ammonium chloride aqueous solution (30 mL) and the mixture was extracted with PFS-2™ (3×20 mL, Ausimont). The extract was dried over anhydrous sodium sulfate and evaporated to dryness by rotary evaporation (60° C.) under pump vacuum evaporated (~5 Torr). A yellow semisolid obtained was mixed with PFS-2™ 20 mL and to this mixture bromine (0.5 mL, 9.76 mmol, Acros) was added via a syringe. The resulting solution was stirred at room temperature for 14 hours. The dark orange solution obtained was washed with acetone (4×20 mL, Fisher Scientific) and evaporated to dryness by rotary evaporation (60° C.) under pump vacuum (~5 Torr). 8.67 Grams of a yellow semisolid product, Bromosilane (A), was obtained (95% yield based on trichlorosilane).

B. The Synthesis of Compound (3)

As shown in Scheme 3, a mixture of Bromosilane (A) and a suspension of SiPc(OH)$_2$ (1.50 g, 2.60 mmol, Aldrich), toluene (150 mL, Fisher Scientific) and pyridine (15 mL, Fisher Scientific), where the toluene and pyridine each had been dried by distillation (~8 mL of distillate), was refluxed for 26 hours, evaporated to dryness by rotary evaporation (60° C.) under pump vacuum (~5 Torr) and mixed with PFS-2™ (50 mL, Ausimont) and Al$_2$O$_3$ III (Neutral, 20 g, Fisher Scientific). The resulting suspension was filtered and the residue was extracted with PFS-2 via a Soxhlet Extractor. The filtrate and extract combined was filtered and the filtrate obtained was evaporated to dryness by rotary evaporation (60° C.) under pump vacuum (1 Torr). A blue, waxy product, Compound (3), was obtained (2.44 gm, 35% yield based on SiPc (OH)$_2$).

An EPD fluid containing 5 wt % of Compound (3) and 6 wt % solid of the TiO$_2$ microcapsules (from Preparation 2) in HT-200 was prepared and evaluated as in Example 1. Contrast ratios of 27-32 were observed at switching voltages of 10-40 V.

Example 4

Synthesis and Evaluation of Fluorinated Silicon Phthalocyanine Compound (4)

The Structure of Compound (4)

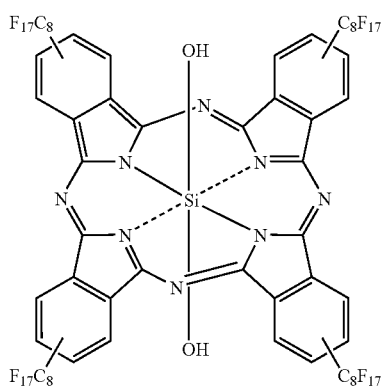

Scheme 4: The synthetic route of Compound (4)

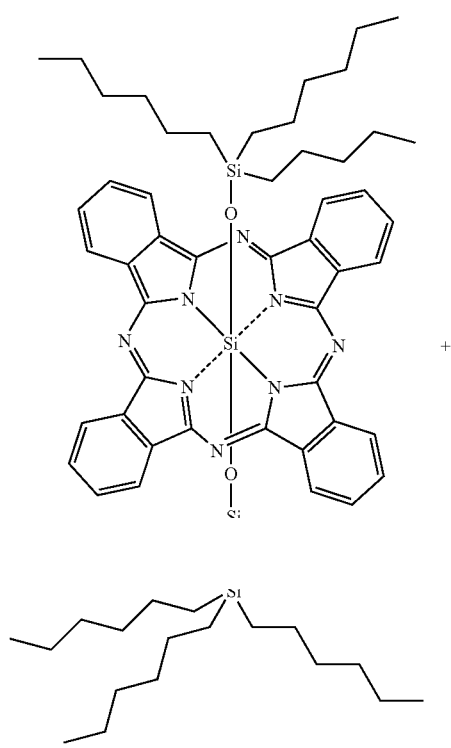

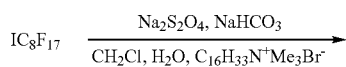

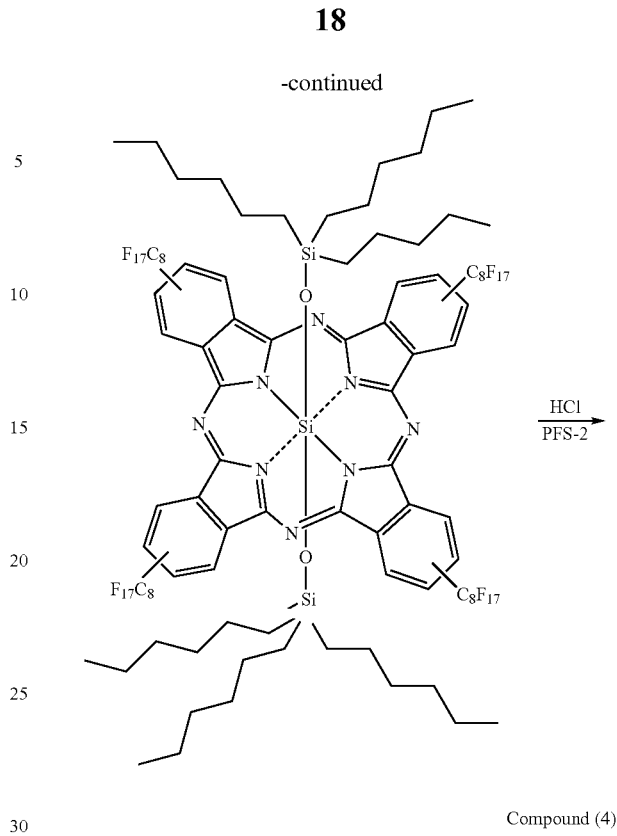

Compound (4)

As shown in Scheme 4, a mixture of sodium dithionite (0.80 g, 4.60 mmol, Fluka) and sodium bicarbonate (0.40 g, 4.76 mmol, Aldrich) was added to a suspension of silicon phthalocyanine bis(trihexylsilyloxide) (0.36 g, 0.30 mmol, Aldrich), cetyl trimethylammonium bromide (0.20 g, Aldrich), 1-iodo-perfluorooctane (4.0 g, 7.33 mmole, Lancaster), $CH_2Cl_2$ (20 mL, HPLC grade, Fisher Scientific) and distilled water (20 mL). The resulting suspension was vigorously stirred at room temperature for 14 hours. Distilled water (20 mL), acetone (10 mL, Fisher Scientific) and PFS-2™ (10 mL, Ausimont) were added into the mixture obtained. The $CH_2Cl_2$ and PFS-2™ layer was separated and washed with water (3×20 mL). A concentrated HCl solution (10 mL, Fisher Scientific) and PFS-2™ (100 mL) were added and the resulting mixture was stirred vigorously at room temperature for 16 hours. The PFS-2™ layer was separated, washed with 20 mL of distilled water three times, dried over anhydrous $Na_2SO_4$ and evaporated to dryness by rotary evaporation (60° C.) under pump vacuum (~5 Torr). The resulting dark blue oil was chromatographed ($Al_2O_3$ III, neutral, Flsher scientific) on a column of dimensions 1.5×15 cm, eluted with PFS-2™ (Ausimont) first and then with ether (HPLC grade, Fisher Scientific). A dark blue product, Compound (4), was obtained (0.062 gm, 9% yield).

An EPD fluid containing 3 wt % of Compound (4) and 6 wt % solid of the $TiO_2$ microcapsules (from Preparation 2) in HT200 was prepared and evaluated as in Example 1. Contrast ratios of 14, 18, and 19 were observed at switching voltages of 10, 20, and 40 V respectively.

Example 5
Synthesis and Evaluation of Fluorinated Silicon Phthalocyanine Compound (5)
The Structure of Compound (5)
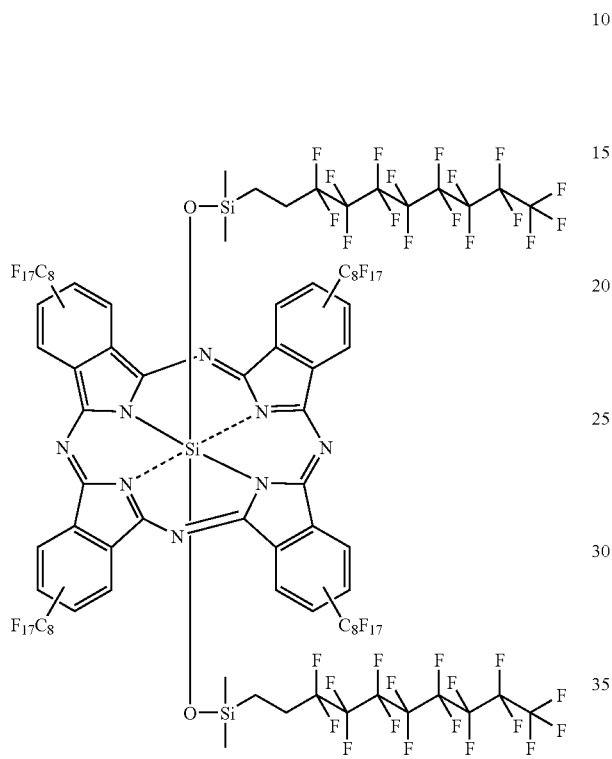
Scheme 5: The synthetic route of Compound (5)
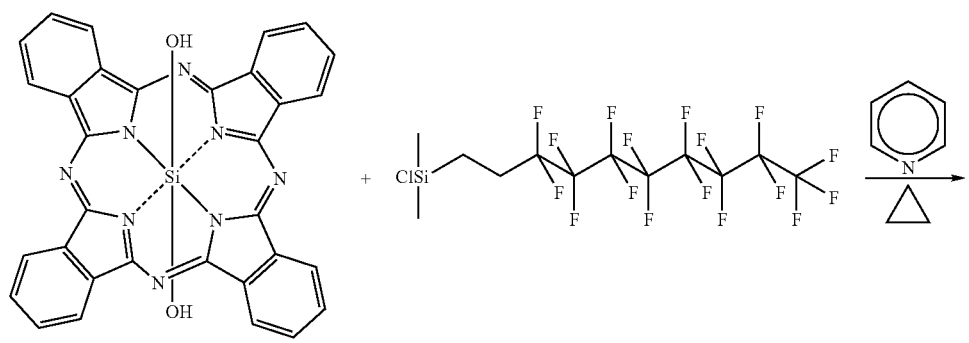

-continued

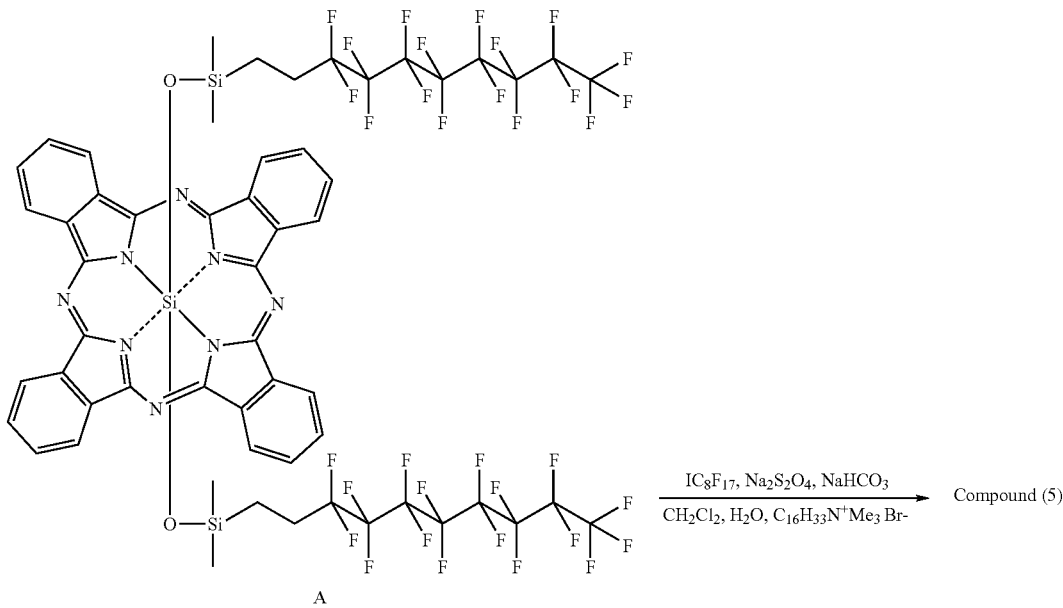

A

A. The Synthesis of SiPc(OSi(CH$_3$)$_2$(CH$_2$)$_2$(CF$_2$)$_7$CF$_3$)$_2$

As shown in Scheme 5, a mixture of (heptadecafluoro-1,1,2,2-tetrahydrodecyl)dimethylchlorosilane (2.50 g, 4.63 mmol, Gelest) and a suspension of SiPc(OH)$_2$ (1.00 g, 1.74 mmol, Aldrich) and pyridine (140 mL, Fisher Scientific), which had been dried by distillation (~10 mL of distillate), was slowly distilled for 5 hours (~55 mL distillate). The resulting dark blue solution was evaporated to dryness by rotary evaporation (60° C.) under pump vacuum (1 Torr). The solid obtained was washed with an EtOH—H$_2$O mixture (1:1, 50 mL) and removed by filtration, dried (60° C., 60 Torr), dissolved in CH$_2$Cl$_2$ (120 mL) and filtered. The filtrate was evaporated to dryness by rotary evaporation (60° C.) under pump vacuum (1 Torr). Phthalocyanine (A), a blue solid (2.26 g, 82% based on SiPc(OH)$_2$), was obtained.

B. The Synthesis of Compound (5)

A mixture of sodium dithionite (1.60 g, 9.19 mmol, Fluka) and sodium bicarbonate (0.80 g, 9.52 mmol, Aldrich) was added into a suspension containing the silicon phthalocyanine and SiPc(OSi(CH$_3$)$_2$(CH$_2$)$_2$(CF$_2$)$_7$CF$_3$)$_2$ (2.26 g, 1.43 mmol) obtained from the procedure 5.A above. To the mixture, 1-iodoperfluorooctane (4.0 g, 7.33 mmol, Lancaster), cetyltrimethylammonium bromide (0.20 g, 0.55 mmol, Aldrich), CH$_2$Cl$_2$ (50 mL) and water (50 mL) were added while stirring vigorously at room temperature. The mixture obtained was kept stirring at room temperature for 18 hours, and then to which water (20 mL) and PFS-2™ (40 mL) were added. The lower organic layer was separated and evaporated to dryness by rotary evaporation (60° C.) under pump vacuum (1 Torr). The dark blue oil obtained was chromatographed using PFS-2™ as the eluent through a column (1×10 cm) packed with Al$_2$O$_3$ III (neutral, Fisher Scientific). The fractions with the blue product were collected and evaporated to dryness by rotary evaporation (60° C.) under vacuum (~5 Torr). Phthalocyanine (A), a blue solid, Compound (5), was obtained (1.41 gm, 30% yield).

An EPD fluid containing 1.8 wt % of Compound (5) and 6 wt % solid of the TiO$_2$ microcapsules (from Preparation 2) in HT-200 was prepared and evaluated as in Example 1. Contrast ratios of 26, 43, 71, and 163 were observed at switching voltages of 5, 10, 20, and 40V, respectively.

Example 6

Comparative Example

The Structure of Compound (6)

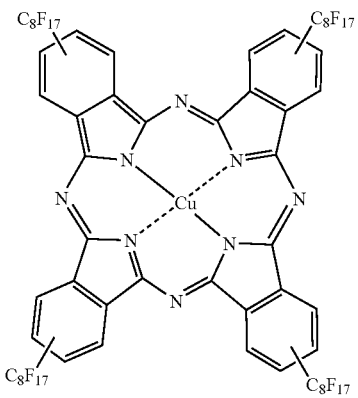

Scheme 6: The synthetic route of Compound (6)

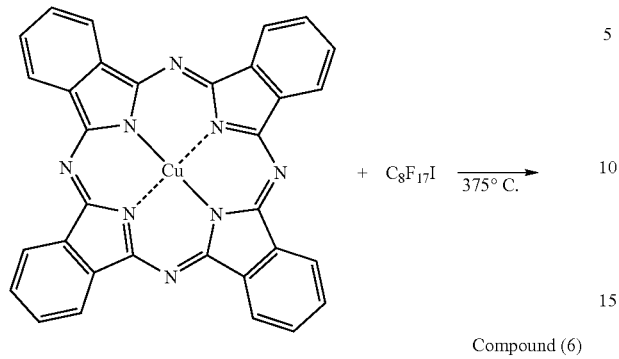

Compound (6)

A fluorinated copper phthalocyanine dye, Compound (6), was prepared according to U.S. Pat. No. 3,281,426 (Scheme 6). A mixture of copper phthalocyanine (41.0 g, 71.2 mmole, Aldrich) and 1-iodoperfluorooctane (370 g, 678 mmole, SynQuest) was added into a 1-gallon pressure reactor (Parr Instrument Co.) with a glass liner. The reactor was vacuum sealed at 1 Torr and heated at 375° C. for 3 days. The crude product obtained was mixed with 200 g of Celite (Fisher Scientific) and extracted with 4 L of PFS-2™ in a Soxhlet extractor for 5 days. The dark blue solution obtained was washed with 4 L of acetone 3 times and evaporated to dryness by rotary evaporation (60° C.) under vacuum (~5 Torr). A dark blue solid, Compound (6), was obtained (106 g, 66% yield).

The maximum solubility of the fluorinated copper phthalocyanine, Compound (6), is about 1.5 wt % in HT-200. An EPD fluid containing 1.5 wt % of Compound (6) and 6 wt % solid of the $TiO_2$ microcapsules (from Preparation 2) in HT-200 was prepared and evaluated as in Example 1. Contrast ratios of 15-17 were observed at switching voltages of 10-40V.

Example 7

Comparative Example 1.0 wt % of a fluorinated copper phthalocyanine blue dye, FC3275 (from 3M Co., MN), was used to replace the 1.5 wt % of Compound (6) in the EPD fluid of Example 6. The maximum solubility of FC3275 in HT-200 was about 1 wt %. Contrast ratios of 6-16 were observed at switching voltages of 40-80V.

As can be seen from the examples, the fluorinated Si phthalocyanine dyes of the present invention showed significant improvement over the fluorinated copper phthalocyanines in both solubility and contrast ratio for EPD applications. Moreover, the dyes, Compounds (1)-(5), also showed acceptable thermal and UV stability for outdoor EPD applications.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, materials, compositions, processes, process step or steps, to the objective, spirit and scope of the present invention. All such modifications are intended to be within the scope of the claims appended hereto.

What is claimed is:

1. An electrophoretic display comprising:
   a) two electrode plates;
   b) an array of display cells filled with an electrophoretic fluid comprising charged pigment particles dispersed in a fluorinated solvent or solvent mixture wherein the fluorinated solvent or solvent mixture is colored by a fluorinated silicon phthalocyanine or silicon naphthalocyanine compound represented by the following formulas:

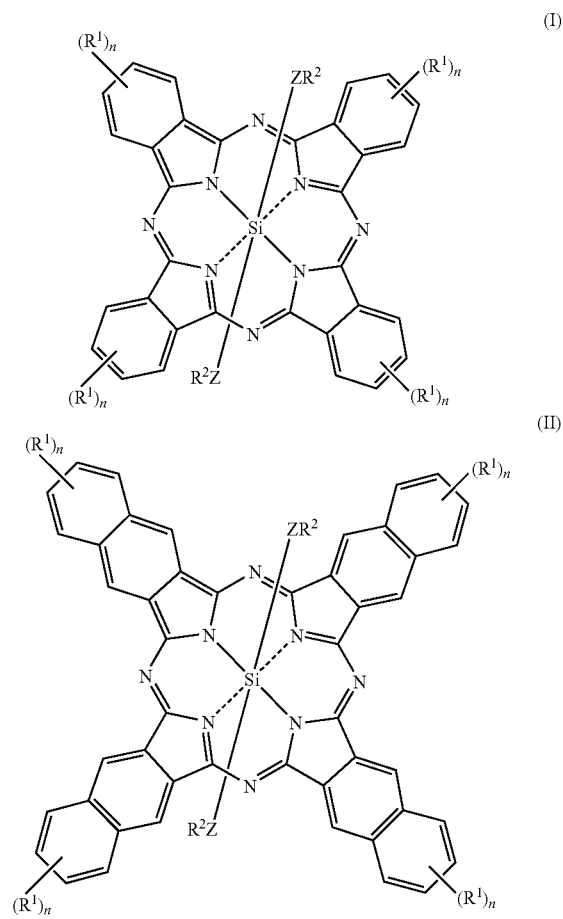

wherein each n is individually 0-4 for silicon phthalocyanine (I) or 0-6 for silicon naphthalocyanine (II);

$R^1$ is independently $R_f$-A-, alkyl, heteroalkyl, aryl, heteroaryl, heteroalkylaryl, alkylheteroaryl, heteroarylalkyl, arylheteroalkyl, R'O—, R'S—, R'R"N—, R'CO—, R'OCO—, R'COO—, R'CONR"—, R'R"NCO—, R'NHCONR"—, $R'SO_2NR"$—, or $R'R"NSO_2$—; or a halogenated derivative of alkyl, heteroalkyl, aryl, heteroaryl, heteroalkylaryl, alkylheteroaryl, heteroarylalkyl, arylheteroalkyl, R'O—, R'S—, R'R"N—, R'CO—, R'OCO—, R'COO—, R'CONR"—, R'R"NCO—, R'NHCONR"—, $R'SO_2NR'$—, or $R'R"NSO_2$—; wherein R' and R" are independently hydrogen, $R_f$, alkyl, heteroalkyl, aryl, heteroaryl, hetarylalkyl, arylheteralkyl, heteroalkylaryl, or alkylheteroaryl;

A is a single bond, —$CH_2O$—, —$CH_2CH_2O$—, or —CO—;

Z is O or NR' wherein R' is defined as above;

$R^2$ is hydrogen, $R_f$—B—, alkyl, heteroalkyl, a halogenated derivative of alkyl, a halogenated derivative of heteroalkyl, or $SiR^3R^4R^5$, wherein $R^3$, $R^4$, and $R^5$ are independently an alkyl or fluoroalkyl group of 1 to 20 carbon atoms or alkoxy or fluoralkoxy of 2 to 40 carbon atoms;

B is a single bond, —$CH_2$—, or —$CH_2CH_2$—;

$R_f$ is a fluorinated polymeric or oligomeric moiety having a molecular weight of 100-100,000 and is prepared from one or more types of fluorinated monomers; provided that the substituents, $R^1$, $R^2$, $R^3$, $R^4$, $R^5$, $R_f$, Z and n are so selected that the total fluorine content of the fluorinated silicon phthalocyanine or silicon napthalocyanine compound is at least 20% by weight, and said charged pigment particles in the electrophoretic fluid are capable of moving towards one or the other electrode plate depending on the voltage difference imposed between the two electrode plates.

2. The electrophoretic display of claim 1, wherein the total fluorine content of said fluorinated silicon phthalocyanine or silicon naphthalocyanine compound is at least 30% by weight.

3. The electrophoretic display of claim 2, wherein the total fluorine content is at least 50% by weight.

4. The electrophoretic display of claim 1, wherein $R_f$ in said fluorinated silicon phthalocyanine or silicon naphthalocyanine compound is prepared from one or more types of the fluorinated monomers selected from the group consisting of epoxide, hydrofuran, cyclolactone, cyclolactam, acrylate, methacrylate, styrene, vinylether and vinylalkane.

5. The electrophoretic display of claim 1, wherein A in said fluorinated silicon phthalocyanine or silicon naphthalocyanine compound is —$CH_2O$—, —$CH_2CH_2O$—, or —CO—.

6. The electrophoretic display of claim 1, wherein B in said fluorinated silicon phthalocyanine or silicon naphthalocyanine compound is —$CH_2$—.

7. The electrophoretic display of claim 1, wherein n in said fluorinated silicon phthalocyanine or silicon naphthalocyanine compound is 0-2.

8. The electrophoretic display of claim 1, wherein $R^1$ in said fluorinated silicon phthalocyanine or silicon naphthalocyanine compound is an alkyl, fluoroalkyl, alkoxy, or fluoralkoxy group having from 1 to 20 carbon atoms.

9. The electrophoretic display of claim 8, wherein $R^1$ in said fluorinated silicon phthalocyanine or silicon naphthalocyanine compound is an alkyl, fluoroalkyl, alkoxy, or fluoralkoxy group having 1 to 12 carbon atoms.

10. The electrophoretic display of claim 1, wherein Z in said fluorinated silicon phthalocyanine or silicon naphthalocyanine compound is oxygen.

11. The electrophoretic display of claim 1, wherein $R^2$ in said fluorinated silicon phthalocyanine or silicon naphthalocyanine compound is hydrogen, $R_f$—$CH_2$—, alkyl, fluoroalkyl, or —$SiR^3R^4R^5$, wherein $R^3$, $R^4$ and $R^5$ are indep alkyl group, a fluorinated alkyl of 6 to 12 carbon atoms, or a fluorinated alkoxy of 6 to 18 carbon atoms.

12. The electrophoretic display of claim 11, wherein $R^2$ is —$SiR^3R^4R^5$ in which one, two or all three of $R^3$, $R^4$ and $R^5$ are methyl.

13. The electrophoretic display of claim 11, wherein the fluoroalkyl is —$(CH_2)_2(CF_2)_5CF_3$ or —$(CH_2)_2(CF_2)_7CF_3$.

14. The electrophoretic display of claim 11, wherein the fluoroalkoxy is —$OCH_2(CF_2)_{12}CF_3$ or —$CH_2(CF_2)_6CF_3$.

15. The electrophoretic display of claim 1, wherein $R_f$ in said fluorinated silicon phthalocyanine or silicon naphthalocyanine compound is a fluorinated polymer or oligomer having a molecular weight of 200-20,000.

16. The electrophoretic display of claim 15, wherein $R_f$ is a fluorinated polymer or oligomer having a molecular weight of 400-10,000.

17. The electrophoretic display of claim 15, wherein $R_f$ is perfluoropolyether or hydrofluoropolyether.

18. The electrophoretic display of claim 15, wherein $R_f$ is poly(chlorotrifluoroethylene).

19. The electrophoretic display of claim 15, wherein $R_f$ is a polymeric chain derived from fluorinated epoxides.

20. The electrophoretic display of claim 19, wherein $R_f$ is —$CF(CF_3)[OCF_2CF(CF_3)]_nF$.

21. The electrophoretic display of claim 1, wherein in said fluorinated silicon phthalocyanine or silicon naphthalocyanine compound n is 0, Z is oxygen and $R^2$ is —$CH_2CF(CF_3)[OCF_2CF(CF_3)]_nF$.

22. The electrophoretic display of claim 1, wherein in said fluorinated silicon phthalocyanine or silicon naphthalocyanine compound n is 0, Z is oxygen and $R^2$ is —$SiR^3R^4R^5$, in which $R^3$ is —$(CH_2)_2(CF_2)_7CF_3$ and $R^4$ and $R^5$ are both —$OCH_2(CF_2)_{12}CF_3$.

23. The electrophoretic display of claim 1, wherein in said fluorinated silicon phthalocyanine or silicon naphthalocyanine compound n is 0, Z is oxygen and $R^2$ is —$SiR^3R^4R^5$, in which $R^3$, $R^4$ and $R^5$ are all —$(CH_2)_2(CF_2)_5CF_3$.

24. The electrophoretic display of claim 1, wherein in said fluorinated silicon phthalocyanine or silicon naphthalocyanine compound, n is 1, $R^1$ is n-$C_8F_{17}$, Z is oxygen, and $R^2$ is hydrogen.

25. The electrophoretic display of claim 1 wherein in said fluorinated silicon phthalocyanine or silicon naphthalocyanine compound n is 1, $R^1$ is n-$C_8F_{17}$, Z is oxygen, and $R^2$ is —$SiR^3R^4R^5$, in which $R^3$ and $R^4$ both methyl and $R^5$ is —$(CH_2)_2(CF_2)_7CF_3$.

* * * * *